United States Patent
Yamazaki

(10) Patent No.: US 11,292,762 B2
(45) Date of Patent: *Apr. 5, 2022

(54) POLYMER INCLUDING POLYMERIZABLE TRIPTYCENE DERIVATIVE COMPOUND AS COMPONENT

(71) Applicant: SEED CO., LTD., Tokyo (JP)

(72) Inventor: Yoshiko Yamazaki, Tokyo (JP)

(73) Assignee: SEED CO., LTD., Tokyo (JP)

( * ) Notice: Subject to any disclaimer, the term of this patent is extended or adjusted under 35 U.S.C. 154(b) by 55 days.

This patent is subject to a terminal disclaimer.

(21) Appl. No.: 16/966,463

(22) PCT Filed: Feb. 1, 2019

(86) PCT No.: PCT/JP2019/003546
§ 371 (c)(1),
(2) Date: Jul. 31, 2020

(87) PCT Pub. No.: WO2019/151462
PCT Pub. Date: Aug. 8, 2019

(65) Prior Publication Data
US 2021/0032388 A1 Feb. 4, 2021

(30) Foreign Application Priority Data
Feb. 2, 2018 (JP) .............................. JP2018-017415

(51) Int. Cl.
| C08F 220/18 | (2006.01) |
| C08F 220/20 | (2006.01) |
| C08F 212/32 | (2006.01) |
| C07C 69/616 | (2006.01) |
| C08F 220/30 | (2006.01) |
| C07C 69/54 | (2006.01) |
| C08F 222/10 | (2006.01) |

(52) U.S. Cl.
CPC ............ *C07C 69/54* (2013.01); *C08F 212/32* (2013.01); *C08F 220/20* (2013.01); *C08F 222/102* (2020.02)

(58) Field of Classification Search
CPC ... C07C 69/616; C07C 69/6161; C07C 69/54; C07C 57/50; C07C 2603/90; C07C 229/24; C07C 59/72; C08F 220/30; C08F 220/20; C08F 220/18; C08F 212/32
See application file for complete search history.

(56) References Cited

U.S. PATENT DOCUMENTS

| 2011/0237804 A1 | 9/2011 | Tanaka et al. | |
| 2017/0022323 A1* | 1/2017 | Swager | C08G 65/4006 |
| 2019/0017726 A1 | 1/2019 | Darby et al. | |
| 2019/0177263 A1 | 6/2019 | Yamazaki | |
| 2020/0369596 A1* | 11/2020 | Yamazaki | C07C 69/616 |
| 2021/0032388 A1* | 2/2021 | Yamazaki | C08F 220/20 |

FOREIGN PATENT DOCUMENTS

| JP | S60-081148 | 5/1985 |
| JP | S63-117013 | 5/1988 |
| JP | 2002-539286 | 11/2002 |
| JP | 2006-111571 | 4/2006 |
| JP | 2006187225 | 7/2006 |
| JP | 2008-075047 | 4/2008 |
| JP | 2008-308433 | 12/2008 |
| JP | 2011-207792 | 10/2011 |
| JP | 2011-246365 | 12/2011 |
| JP | 2013223458 | 10/2013 |
| JP | 2014-178712 | 9/2014 |
| WO | 00-53655 A1 | 9/2000 |
| WO | 2018025892 | 2/2018 |

OTHER PUBLICATIONS

Barros et al "Bridgehead-Substituted Triptycenes for Discovery of Nucleic Acid Junction Binders" Org. Lett. 2016, 18, 10, 2423-2426 Publication Date:May 12, 2016 as seen online at https://doi.org/10.1021/acs.orglett.6b00945.

Hoffmeister et al "Triptycene polymers" Journal of Polymer Science Part A-1: Polymer Chemistry,vol. 7, Issue1, Jan. 1969, pp. 55-72 as seen online at https://doi.org/10.1002/pol.1969.150070107.

Brunovlenkaya, I. I. et al., Aromatic hydrocarbons. LXIII. Intramolecular cyclization in the triptycene series, Zhumal Organicheskoi Khimii, 1979, vol. 15, No. 7, p. 1502-1506, particularly, p. 1503, compound I, p. 1504, compounds IX-XI.

Notification concerning transmittal of international preliminary report on patentability (Form PCT/IB/326).

International preliminary report on patentability (Form PCT/IB/373).

Notification of transmittal of translation of the international preliminary report on patentability (Form PCT/IB/338).

Translation of International preliminary report on patentability (Form PCT/IB/373).

(Continued)

*Primary Examiner* — Robert D Harlan

(74) *Attorney, Agent, or Firm* — JMB Davis Ben-David

(57) ABSTRACT

It is an objective of the present invention to provide a polymer compound as constituent component a polymerizable triptycene derivative and that has a structure in which three benzene rings arranged at the axis formed by barrelene of the triptycene skeleton can rotate evenly and that has hydrophilicity imparted to it as compared to any of the prior art triptycene derivatives and is thus highly useful in functional materials.

The above objective is achieved by the polymerizable triptycene derivative and a polymer compound as constituent component thereof having substituents with an unsaturated bonding functional group at position 9 and/or position 10 of the triptycene skeleton, the polymerizable triptycene derivative having two carboxyl groups and the polymerizable triptycene derivative having one carboxyl group and one amino group.

3 Claims, No Drawings

(56) References Cited

OTHER PUBLICATIONS

Extended European Search Report of corresponding EP patent application (19748198.9) [9 pages].
Ates, S., Aydogan, B., Torun, L. and Yagci, Y., 2010. Synthesis and characterization of triptycene type cross-linker and its use in photoinduced curing applications. Polymer, 51(4), pp. 825-831.

* cited by examiner

POLYMER INCLUDING POLYMERIZABLE TRIPTYCENE DERIVATIVE COMPOUND AS COMPONENT

CROSS-REFERENCE TO RELATED APPLICATIONS

This is the US National Stage of International Patent Application No. PCT/JP2019/003546, filed Feb. 1, 2019, which in turn claims the benefit of priority to Japanese Patent Application No. 2018-17415, filed Feb. 2, 2018, the disclosure of which is incorporated herein by reference in its entirety.

TECHNICAL FIELD

The present invention relates to a polymer compound containing a triptycene derivative having a substituted triptycene structure as constituent component.

BACKGROUND ART

A polymer compound can be obtained by polymerization of one or combination of two or more of polymerizable compounds such as (meth)acrylic acids and their derivatives as monomer components or by polycondensation of compounds having a dicarboxylic acid or compounds having an amino group and a carboxylic group within the molecules.

The characteristics of the polymer compound can vary widely depending on the monomer compounds used as constituent materials or their combinations. Hence, it is necessary to take into consideration such combinations of monomer compounds used as constituent materials or provision of novel monomer compounds for use as constituent materials in order to obtain polymer compounds having new characteristics or polymer compounds having some of their known characteristics improved. To provide novel monomer compounds, known compounds may be chemically modified at specific sites or polymerizable functional groups may be added.

Triptycene is an aromatic hydrocarbon having a paddle wheel-like structure in which three benzene rings are arranged in a manner similar to paddles of a paddle wheel to give $D_{3h}$ symmetry. Because of such a structure, application of triptycene in various functional materials has been contemplated. Several triptycene derivatives that have a triptycene structure (skeleton) are also known.

Among known such compounds are, for example, compounds formed by ring fusion of triptycene skeleton with further other ring structures (See Patent Document 1 below, the disclosure of which is incorporated herein by reference in its entirety), optically active triptycene derivatives obtained by asymmetric acylation with enzymes (See Patent Document 2 below, the disclosure of which is incorporated herein by reference in its entirety), and optically active triptycene derivatives obtained by reacting a mixture of optical isomers of a triptycene derivative having hydrolyzable functional groups with a hydrolase capable of asymmetric hydrolysis (See Patent Document 3 below, the disclosure of which is incorporated herein by reference in its entirety).

Also known are a photoresist substrate and a photoresist composition in which a triptycene derivative with a specific structure are oriented (See Patent Document 4 below, the disclosure of which is incorporated herein by reference in its entirety); a triptycene ring-containing liquid crystal compound that exhibits a good compatibility with other liquid crystal compounds, has a small phase shift or a small chromatic dispersion of optical anisotropy, and has polymerizability (See Patent Document 5 below, the disclosure of which is incorporated herein by reference in its entirety); a triptycene group-containing polymer electroluminescence material having, optionally substituted, vinylene group, ethynylene group, arylene group, heteroarylene group and spirobifluorene group (See Patent Document 6 below, the disclosure of which is incorporated herein by reference in its entirety); a triptycene-containing compound that is one of compounds having a polymerizable group and a 1,4-dimethylenecyclohexane backbone, and that has a liquid crystal phase and exhibits a good compatibility with other liquid crystal compounds and organic solvents (See Patent Document 7 below, the disclosure of which is incorporated herein by reference in its entirety); and a triptycene-containing compound that is one of liquid crystal display element compounds that are composed of a photopolymerizable monomer and/or oligomer selected from a polyimide consisting of a diamine and a tetracarboxylic acid dianhydride or a polyamic acid derivative, a precursor of the polyimide (See Patent Document 8 below, the disclosure of which is incorporated herein by reference in its entirety).

Further known is a triptycene derivative having a structure consisting of a barrelene having a plurality of unsaturated polymerizable functional groups attached thereto, including a triple bond-containing functional group and a double bond-containing functional group (See Patent Document 9 below, the disclosure of which is incorporated herein by reference in its entirety).

PRIOR ART DOCUMENT

Patent Document

Patent Document 1: JP 2011-207792 A
Patent Document 2: JP 2013-223458 A
Patent Document 3: JP 2006-187225 A
Patent Document 4: JP 2008-308433 A
Patent Document 5: JP 2006-111571 A
Patent Document 6: JP 2002-539286 A
Patent Document 7: JP 2011-246365 A
Patent Document 8: JP 2014-178712 A
Patent Document 9: JP 2008-075047 A

SUMMARY OF INVENTION

Technical Problem

Because most of the prior art triptycene derivatives have a structure in which a polymerizable group for forming a polymer extension chain has been incorporated into an aromatic ring of the triptycene skeleton, it is likely that the rotation of the polymer about an axis formed by barrelenes each having fused three benzene rings is hindered. On the other hand, such a rotation is less likely to be hindered in the triptycene derivative as described in Patent Document 9 since unsaturated polymerizable functional groups are at positions 9 and 10 of the triptycene.

However, the hydrophobic nature of alkenyl and alkynyl groups used as the unsaturated polymerizable functional groups in the triptycene derivative as described in Patent Document 9, as well as hydrophobic nature of triptycene itself, makes the overall triptycene derivative as described in Patent Document 9 hydrophobic. Because of this characteristic, the triptycene derivative as described in Patent Document 9 has limited applications in compositions for use as functional materials and is thus less useful.

There is no known the polymerizable triptycene derivatives or the polymer compounds containing as constituent component the polymerizable triptycene derivatives that can solve the problems of the above-described prior art.

Hence, it is an objective of the present invention to provide a novel polymer compound containing as constituent component a polymerizable triptycene derivative that has a structure permitting even rotation of the three benzene rings arranged about the axis formed by barrelenes of the triptycene backbone and that has hydrophilicity imparted to it as compared to any of the prior art triptycene derivatives and is thus highly useful in functional materials.

Solution to Problem

In an effort to provide the above-described novel polymerizable triptycene derivatives, the present inventors have focused on the type and attached positions of polymerizable functional groups involved in the polymerization reaction. The present inventors have postulated that in order for the three benzene rings to rotate evenly, it is desirable that the three benzene rings rotate about the barrelene to which they are attached. The present inventors have further postulated that a polymerizable triptycene derivative having compatibility with other hydrophilic compounds can be provided by selecting hydrophilic functional groups as polymerizable functional groups to be introduced.

Based on the above-described considerations, the present inventors have conducted extensive studies and after many trials and failures, have succeeded in producing a compound that has hydrophilic polymerizable functional groups at position 9 and/or position 10 of the triptycene skeleton. This compound is a polymerizable triptycene derivative having a structure that permits even rotation of the three benzene rings arranged about the axis formed by barrelene in the triptycene skeleton and has hydrophilicity imparted to it as compared to any of the prior art polymerizable triptycene derivatives. Thus, the compound can serve as a highly useful functional material. A patent application has been filed for a part of the novel polymerizable triptycene derivatives completed in this manner as Patent Application JP 2016-152953.

The present inventors have succeeded in producing a polymer compound with increased compatibility with the other compound capable of copolymerizing and forming a good hydrogel by using the polymerizable triptycene derivative having (meth)acryloyl oxyalkyl group at position 9 and/or position 10 of the triptycene skeleton. These findings and successful examples have ultimately led to the completion of the present invention.

According to one embodiment of the present invention, there is provided a polymer compound containing as constituent component:
a polymerizable triptycene derivative represented by the following general formula (1), and

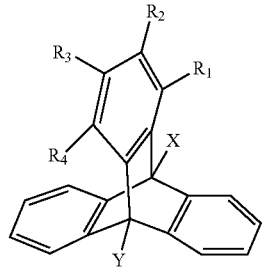

(wherein
$R_1$ to $R_4$ are each independently a substituent selected from the group consisting of hydrogen atom, alkyl group, cycloalkyl group, heterocyclic group, alkenyl group, cycloalkenyl group, alkynyl group, alkoxy group, alkylthio group, arylether group, arylthioether group, aryl group, heteroaryl group, halogen atom, carbonyl group, carboxyl group, oxycarbonyl group, carbamoyl group, amino group, phosphineoxide group, and silyl group, with the proviso that adjacent substituents may together form a ring; one of X and Y is a substituent represented by the following general formula (2):

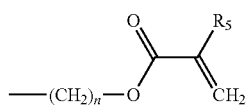

(wherein n is an integer of 1 to 5; and $R_5$ shows hydrogen atom or methyl group.)
and the other of X and Y is a substituent selected from the group consisting of the substituents represented by the general formula (2), hydrogen atom and halogen atom, and protected or unprotected hydroxyl group, hydroxylalkyl group, carboxyl group, carboxylalkyl group, amino group, aminoalkyl group, aminocarbonyl group, aminocarbonylalkyl group, alkoxy group, alkoxyalkyl group, alkoxycarbonyl group, alkoxycarbonylalkyl group, formyl group, formylalkyl group, and alkyl group.)
a compound capable of copolymerizing with the polymerizable triptycene derivative.

Preferably, the other of X and Y is a substituent selected from the group consisting of the substituents represented by the following general formula (3):

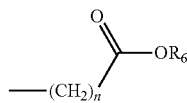

(wherein n is an integer of 1 to 5; and $R_6$ is a substituent selected from the group consisting of hydrogen atom and alkyl group having any one of carbons 1 to 3),
the substituents represented by the following formula (4):

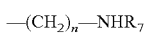

(wherein n is an integer of 1 to 5; and $R_7$ is a substituent selected from the group consisting of hydrogen atom and a carbamate protective group), and the substituents represented by the following general formula (5):

—(CH$_2$)$_n$—OH  (5)

(wherein n is an integer of 1 to 5).

Preferably, the compound capable of copolymerizing with the polymerizable triptycene derivative is at least one hydrophilic compound.

Advantageous Effects of Invention

Polymerizable triptycene derivatives used in polymer compounds in one embodiment of the present invention have a structure in which polymerizable functional groups are attached to carbons of barrelene, which forms a main skeleton of triptycene, such that each of the three benzene rings in the triptycene structure can rotate evenly about an axis formed by the barrelene. Furthermore, the polymerizable triptycene derivatives are compatible with not only hydrophobic compounds but also with hydrophilic compounds due to introducing functional groups having hydrophilicity. Thus, the polymer compound in one embodiment of the present invention can be a polymer compound with various functions different from conventional compounds. In particular, the polymer compound in one embodiment of the present invention can be used to produce hydrogels swollen by hydration, which were not achieved by any of prior art techniques.

Furthermore, since the three benzene rings in the triptycene structure in the polymer compound in one embodiment of the present invention can rotate evenly about the axis formed by barrelene, when a material is encapsulated within the polymer compound, it is expected to control the rate and the extent of diffusion of the encapsulated material released from the polymer compound.

DESCRIPTION OF EMBODIMENTS

While polymer compounds containing as constituent component polymerizable triptycene derivatives in one embodiment of the present invention will now be described in further details, the technical scope of the present invention is not limited to what is described in this section; rather, the present invention may take various other forms to the extent that its objectives are achieved.

The polymer compounds in one embodiment of the present invention are contained as constituent component: a polymerizable triptycene derivative and a compound capable of copolymerizing with the polymerizable triptycene derivative.

The polymerizable triptycene derivatives are represented by the following general formula (1).

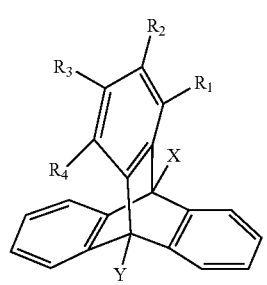
(1)

In the general formula (1), R$_1$ to R$_4$ are each independently selected from the group consisting of hydrogen atom, alkyl group, cycloalkyl group, heterocyclic group, alkenyl group, cycloalkenyl group, alkynyl group, alkoxy group, alkylthio group, arylether group, arylthioether group, aryl group, heteroaryl group, halogen atom, carbonyl group, carboxyl group, oxycarbonyl group, carbamoyl group, amino group, phosphineoxide group, and silyl group. Any adjacent substituents of R$_1$ to R$_4$ may together form a ring.

In the general formula (1), one of X and Y is a substituent represented by the following general formula (2):

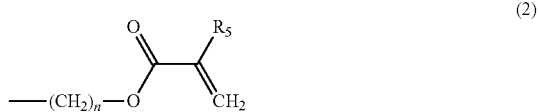
(2)

In the general formula (2), n is an integer of 1 to 5; and R$_5$ shows hydrogen atom or methyl group.

In the general formula (1), one of X and Y is a substituent represented by the general formula (2) and the other substituent is a substituent selected from the group consisting of the substituents represented by the general formula (2), hydrogen atom and halogen atom, and protected or unprotected hydroxyl group, hydroxylalkyl group, carboxyl group, carboxylalkyl group, amino group, aminoalkyl group, aminocarbonyl group, aminocarbonylalkyl group, alkoxy group, alkoxyalkyl group, alkoxycarbonyl group, alkoxycarbonylalkyl group, formyl group, formylalkyl group, and alkyl group. As used herein, the term "protected substituent" is not particularly limited as long as referring to any substituent having any protective group.

The other substituent in the general formula (1) is preferably any of substituents represented by the general formula (2), substituents represented by the general formula (3), substituents represented by the general formula (4) or substituents represented by the general formula (5) as described below.

(3)

In the general formula (3), n is an integer of 1 to 5; and R$_6$ is a substituent selected from the group consisting of hydrogen atom and alkyl group having any one of carbons 1 to 3.

—(CH$_2$)$_n$—NHR$_7$  (4)

In the general formula (4), n is an integer of 1 to 5; and R$_7$ is a substituent selected from the group consisting of hydrogen atom and a carbamate protective group.

—(CH$_2$)$_n$—OH  (5)

In the general formula (5), n is an integer of 1 to 5.

Specific embodiments of the polymerizable triptycene derivatives represented by the general formula (1) include, but are not limited to, polymerizable triptycene derivatives in which X and Y are each independently a substituent shown in Table 1 below. In cases where both X and Y are substituents represented by the general formula (2) as in compound E, they may be an identical substituent or they may be substituents that differ from each other.

TABLE 1

| compound | X | Y |
|---|---|---|
| A | general formula (2) | hydrogen atom |
| B | general formula (2) | general formula (3) |
| C | general formula (2) | general formula (4) |
| D | general formula (2) | general formula (5) |
| E | general formula (2) | general formula (2) |

In any of the polymerizable triptycene derivatives shown in Table 1, $R_1$ to $R_4$ may be all different substituents, or two, three, or all four of them may be an identical substituent.

While the substituent exemplified for $R_1$ to $R_7$ may be not particularly limited as long as any substituent that has a commonly known meaning, for example, it may be a substituent as exemplified below. In addition, the substituent exemplified for $R_1$ to $R_7$ may bear a further substituent. Examples of the further substituent include, but are not particularly limited to, alkyl group, cycloalkyl group, aryl group and heteroaryl group.

Examples of the alkyl group include, but are not limited to, saturated aliphatic hydrocarbon groups, such as methyl group, ethyl group, n-propyl group, isopropyl group, n-butyl group, sec-butyl group, and tert-butyl group. While the alkyl group may have any number of carbons, it preferably has for example from 1 to 20, more preferably from 1 to 8, and still more preferably from 1 to 3 carbons. Examples of the alkyl group bearing a substituent include, but are not limited to, hydroxyalkyl group, aminoalkyl group, carboxyalkyl group, and formylalkyl group.

Examples of the cycloalkyl group include, but are not limited to, saturated alicyclic hydrocarbon groups, such as cyclopropyl group, cyclohexyl group, norbornyl group, and adamantyl group. While the cycloalkyl group may have any number of carbons, it preferably has from 3 to 20 carbons.

Examples of the heterocyclic group include, but are not limited to, alicyclic rings that contain an atom other than carbon atom, such as nitrogen and sulfur atom, including, for example, pyran ring, piperidine ring, cyclic amide. While the heterocyclic group may have any number of carbons, it preferably has from 2 to 20 carbons.

Examples of the alkenyl include, but are not limited to, unsaturated aliphatic hydrocarbon groups having a double bond, such as vinyl group, allyl group, and butadienyl group. While the alkenyl group may have any number of carbons, it preferably has from 2 to 20 carbons.

Examples of the cycloalkenyl group include, but are not limited to, unsaturated alicyclic hydrocarbon groups having a double bond, such as cyclopentenyl group, cyclopentadienyl group, and cyclohexenyl group.

Examples of the alkynyl group include, but are not limited to, unsaturated aliphatic hydrocarbon groups having a triple bond, such as ethynyl group. While the alkynyl group may have any number of carbons, it preferably has from 2 to 20 carbons.

Examples of the alkoxy group include, but are not limited to, functional groups with an aliphatic hydrocarbon group attached via an ether linkage, including, for example, methoxy group, ethoxy group, and propoxy group. While the alkoxy group may have any number of carbons, it preferably has from 1 to 20 carbons. Examples of the alkoxy group bearing a substituent include, but are not limited to, alkoxyalkyl group, alkoxycarbonyl group, and alkoxycarbonylalkyl group.

Examples of the alkylthio group include, but are not limited to, functional groups in which the oxygen atom of their ether bond in alkoxy groups is replaced with a sulfur atom. While the alkylthio group may have any number of carbons, it preferably has from 1 to 20 carbons.

Examples of the arylether group include, but are not limited to, functional groups having an aromatic hydrocarbon group attached via an ether linkage, such as phenoxy group. While the arylether group may have any number of carbons, it preferably has from 6 to 40 carbons.

Examples of the alkylthioether group include, but are not limited to, functional groups in which the oxygen atom of their ether bond in arylether groups is replaced with a sulfur atom. While the arylthioether group may have any number of carbons, it preferably has from 6 to 40 carbons.

Examples of the aryl group include, but are not limited to, aromatic hydrocarbons, such as phenyl group, naphthyl group, biphenyl group, anthracenyl group, phenanthryl group, terphenyl group, and pyrenyl group. While the aryl group may have any number of carbons, it preferably has from 6 to 40 carbons.

Examples of the heteroaryl group include, but are not limited to, 5-membered cyclic aromatic groups with their rings containing one atom other than carbon, such as furanyl group, thiophenyl group, benzofuranyl group and dibenzofuranyl group, and 6-membered cyclic aromatic groups with their rings containing one or more atoms other than carbon, such as pyridyl group and quinolynyl group. While the heteroaryl group may have any number of carbons, it preferably has from 2 to 30 carbons.

Examples of halogen atom include, but are not limited to, fluorine, chlorine, bromine, and iodine.

Each of the carbonyl group, carboxyl group, oxycarbonyl group, carbamoyl group, amino group, formyl group, and phosphine oxide group may bear a substituent, which in turn may bear a further substituent. Examples of the amino group bearing a substituent include, but are not limited to, aminocarbonyl group, and aminocarbonylalkyl group.

Examples of the silyl group include, but are not limited to, functional groups having a silicon atom bonded to them, such as trimethylsilyl group. While the silyl group may have any number of carbons, it preferably has from 3 to 20 carbons. While the silyl may have any number of silicons, it preferably has from 1 to 6 silicons.

Any adjacent substituents of the substituents represented by $R_1$ to $R_4$, that is, $R_1$ and $R_2$, $R_2$ and $R_3$, and/or $R_3$ and $R_4$ may together form a ring (i.e., fused ring). In other words, the fused ring is formed by any adjacent two substituents selected from $R_1$ to $R_4$ (e.g., $R_1$ and $R_2$) that are bound together to form a conjugated or unconjugated fused ring. Examples of the constituent elements involved in the formation of a fused ring include, but are particularly not limited to, carbon atom, nitrogen atom, oxygen atom, sulfur atom, phosphorus atom, and silicon atom. The substituents represented by $R_1$ to $R_4$ may be further fused with another ring.

Examples of the carbamate protective group include, but are not limited to, carbamate protective groups such as tert-butoxycarbonyl group, benzyloxycarbonyl group, 9-fluorenylmethyloxycarbonyl group, 2,2,2-trichloroethoxycarbonyl group, and allyloxycarbonyl group.

More specific embodiments of the polymerizable triptycene derivatives represented by the general formula (1)

include, but are not limited to, for example, compounds of the following formulas (6), (7), (8), (9), (10), (11) and (12), where Me in the formula represents methyl group:

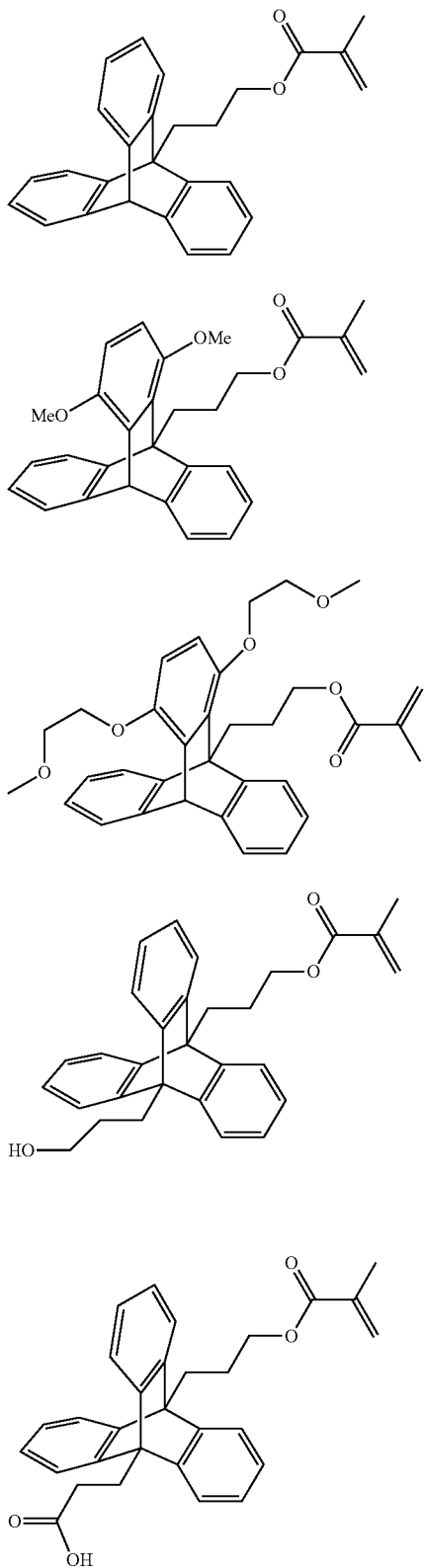

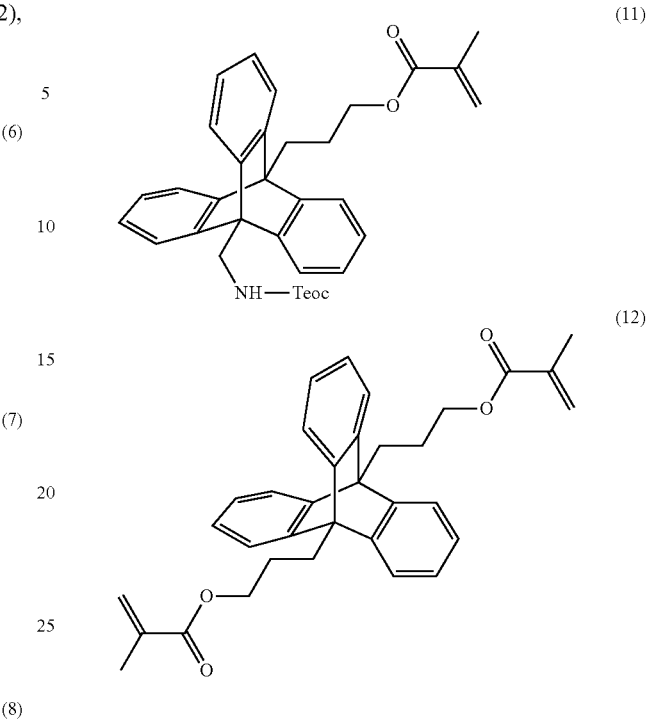

While the polymerizable triptycene derivative of the present invention may be produced by any method that is not particularly limited, it may be produced for example by using any of the methods described later in Examples or by modifying these methods as desired to obtain desired polymerizable triptycene derivatives.

One embodiment of the production method of a polymerizable triptycene derivative of the general formula (1) includes, but not limited to, a method including: subjecting 9-halogen anthracene or 9,10-dihalogen anthracene and an acetal compound having a vinyl group to Heck coupling reaction and hydrolysis; subjecting the resulting reaction product and benzyne to Diels-Alder reaction and, optionally, to a reaction for modifying substituents born by benzyne; subjecting the resulting reaction product to reduction with a metal hydride; and subjecting the resulting reaction product to a reaction with a halogenated (meth)acryloyl to obtain a triptycene derivative having a (meth)acryloyl oxyalkyl group as a polymerizable triptycene derivative of the general formula (1).

Another embodiment of the production method of a polymerizable triptycene derivative of the general formula (1) includes, but not limited to, a method including: subjecting 9-halogen anthracene or 9,10-dihalogen anthracene and an acetal compound having a vinyl group to a Heck coupling reaction and hydrolysis; subjecting the resulting reaction product and benzyne to a Diels-Alder reaction and, optionally, to a reaction for modifying substituents born by benzyne; and subjecting the resulting reaction product to an alkali treatment and an acid treatment to obtain a polymerizable triptycene derivative of the general formula (1) in which at least one of X or Y is a substituent represented by the general formula (3).

Another embodiment of the production method of a polymerizable triptycene derivative of the general formula (1) includes, but not limited to, a method including: subjecting 9-halogen anthracene or anthracene and an amide compound to a Vilsmeier-Haack reaction; subjecting the resulting reaction product and a primary amine having a carbamate protective group to an amine addition reaction; subjecting the resulting reaction product and benzyne to Diels-Alder reaction and, optionally, to a reaction for modifying substituents born by benzyne; and, optionally, subjecting the resulting reaction product to an alkali treatment and an acid treatment to obtain a polymerizable triptycene derivative of general formula (1) in which at least one of X or Y is a substituent represented by the general formula (4).

One embodiment of the production method of a polymerizable triptycene derivative of the general formula (1) includes, but not limited to, a method including: subjecting 9-halogen anthracene or 9,10-dihalogen anthracene and an acetal compound having a vinyl group to Heck coupling reaction and hydrolysis; subjecting the resulting reaction product and benzyne to Diels-Alder reaction; and subjecting reaction with methacryloly chloride to obtain a polymerizable triptycene derivative of the general formula (1) in which at least one of X or Y is a substituent represented by the general formula (5).

Also, a polymerizable triptycene derivative of the general formula (1) in which both X and Y are substituents represented by the general formula (2); a polymerizable triptycene derivative of the general formula (1) in which one of X and Y is a substituent represented by the general formula (2) and the other of X and Y is a substituent represented by the general formula (3); a polymerizable triptycene derivative of the general formula (1) in which one of X and Y is a substituent represented by the general formula (2) and the other of X and Y is a substituent represented by the general formula (4); or a polymerizable triptycene derivative of the general formula (1) in which one of X and Y is a substituent represented by the general formula (2) and the other of X and Y is a substituent represented by the general formula (5); can be obtained by combining the above-described two embodiments of the production method of a polymerizable triptycene derivative of the above general formula (1).

The polymer compound in one embodiment of the present invention may be formed by subjecting one or combination of two or more of above-mentioned polymerizable triptycene derivatives of the general formula (1) and a compound capable of copolymerizing with the derivatives to a copolymerization reaction.

The preferable amount of the polymerizable triptycene derivative of the general formula (1) in the polymer compound in one embodiment of the present invention is not particularly limited, but is, for example, 0.1 wt % to 25 wt % relative to the total amount of the polymer compound, preferably 0.5 wt % to 20 wt %, more preferably 1 wt % to 15 wt %. When the amount of the polymerizable triptycene derivative of the general formula (1) is less than 0.1 wt %, the effect of the triptycene structure is less likely to be exhibited in the obtained polymer compound. When the amount of the polymerizable triptycene derivative of the general formula (1) exceeds 25 wt %, it is undesirable because the obtained polymer compound is prone to cloudiness and loss of strength.

The compound capable of copolymerizing with the polymerizable triptycene derivative of the general formula (1) in the polymer compound in one embodiment of the present invention is not particularly limited as long as it can be a monomer component as is generally known, but for example, a hydrophilic compound is preferably used. In the resulting polymer compound obtained by using the hydrophilic compound, each of the three benzene rings in the triptycene structure can rotate evenly about the axis formed by barrelene and the introduced polymerizable functional groups are hydrophilic groups. Thus, the polymer compound can encapsulate a hydrophilic material or a hydrophobic material and it is possible to control the rate and the extent of diffusion of the encapsulated material when it is released from the polymer compound. The polymer compound with such characteristics can be used in a variety of applications, including, for example, liquid crystal alignment film, liquid crystal display elements, organic EL displays, organic thin films with electron transporting properties, light-emitting elements and organic conductive compositions, as well as hydrogels, medical devices, ophthalmic lenses and DDS devices.

The hydrophilic compound capable of copolymerizing with the polymerizable triptycene derivative of the general formula (1) is not particularly limited as long as it can be a hydrophilic monomer component as is generally known, and examples thereof include (meth)acrylic monomers such as N, N-dimethylacrylamide, 2-hydroxyethyl methacrylate, (meth)acrylic acid, polyethylene glycol monomethacrylate, and glycerol methacrylate; and vinyl monomers such as N-vinyl pyrrolidone, N-vinyl-N-methylacetamide, N-vinyl-N-ethylacetamide, N-vinyl-N-ethylformamide, and N-vinyl-formamide, and one or two or more of these can be used alone or in combination. The amount of the hydrophilic compound capable of copolymerizing with the polymerizable triptycene derivative of the general formula (1) is not particularly limited, but is, for example, 75 wt % to 99.9 wt % relative to the total amount of the polymer compound, preferably 80 wt % to 99.5 wt %, and more preferably 75 wt % to 99 wt %. Depending on the type and amount of hydrophilic compound capable of copolymerizing with the polymerizable triptycene derivative of the general formula (1), it is possible to obtain the polymer compound with the desired flexibility and water content.

In order to impart strength, shape stability and flexibility to the polymer compound in one embodiment of the present invention, it can be used linear, branched-chain or cyclic alkyl(meth)acrylates such as methyl(meth)acrylate, ethyl (meth)acrylate, propyl(meth)acrylate, i-propyl(meth)acrylate, n-butyl(meth)acrylate, i-butyl(meth)acrylate, t-butyl (meth)acrylate, 2-ethylhexyl(meth)acrylate, cyclohexyl (meth)acrylate, methoxydiethyleneglycol(meth)acrylate, ethoxydiethyleneglycol(meth)acrylate, phenyl(meth)acrylate, phenoxyethyl(meth)acrylate, benzyl(meth)acrylate, isobonyl(meth)acrylate as a hydrophobic compound capable of copolymerizing with the polymerizable triptycene derivative of the general formula (1). According to desired physical properties, one or two or more of the hydrophobic compounds can be appropriately blended alone or in combination. The amount of the hydrophobic compound capable of copolymerizing with the polymerizable triptycene derivative of the general formula (1) is not particularly limited, but is, for example, 0 wt % to 30 wt % relative to the total amount of the polymer compound, and preferably 0 wt % to 20 wt %. When the amount of the hydrophobic compound capable of copolymerizing with the polymerizable triptycene derivative of the general formula (1) exceeds 30 wt %, the strength, shape stability, or flexibility of the obtained polymer compound may be reduced.

In order to impart heat resistance and mechanical properties to the polymer compound in one embodiment of the present invention, cross-linkable compounds such as a (meth)acrylate-based cross-linkable compound and a vinyl-based cross-linkable compound can be used as a constituent. Examples of the (meth)acrylate-based cross-linkable compound include ethylene glycol di(meth)acrylate, diethylene glycol di(meth)acrylate, triethylene glycol di(meth)acrylate, propylene glycol di(meth)acrylate, dipropylene glycol di(meth)acrylate, trimethylol propantri(meth)acrylate, pentaerythritol tri(meth)acrylate. Examples of the vinyl-based cross-linkable compound include allyl (meth)acrylate, diaryl maleate, diaryl fumarate, diaryl succinate, diaryl phthalate, triaryl cyanurate, triaryl isocyanurate, diethylene glycol bis-allyl carbonate, triaryl phosphate, triaryl trimethylate, diaryl ether, N, N-diaryl melamine, divinylbenzene. According to desired physical properties, one or two or more of the cross-linkable compounds can be appropriately blended alone or in combination. The amount of the cross-linkable compound is not particularly limited, but is, for example, 0.01 wt % to 10 wt % relative to the total amount of the polymer compound, and preferably 0.05 wt % to 3 wt %. When the amount of the cross-linkable compound exceeds 10 wt %, the flexibility of the obtained polymer compound may be reduced.

The polymer compound in one embodiment of the present invention can be produced by combining steps known to those skilled in the art, and the production method is not particularly limited, but can include, for example, the following steps; a step of obtaining a monomer mixture by adding a polymerization initiator to a mixture of monomer compounds such as the polymerizable triptycene derivative of the general formula (1) which is a as constituent component, the hydrophilic compound capable of copolymerizing with the polymerizable triptycene derivative of the general formula (1), the hydrophobic compound capable of copolymerizing with the polymerizable triptycene derivative of the general formula (1) and the cross-linkable compound, stirring and dissolving; and a step of putting the resulting monomer mixture into the desired molding mold and obtaining a copolymer by a copolymer reaction; a step of obtaining a polymer compound as a hydrogel by hydrating and swelling the molded copolymer after cooling, peeling the copolymer from the molding mold, and cutting and, optionally polishing.

Examples of the polymerization initiator include peroxide polymerization initiators such as lauroyl peroxide, cumene hydroperoxide and benzoyl peroxide, which are general radical polymerization initiators; azo polymerization initiators such as azobis dimethylvaleronitrile and azobis isobutyronitrile (AIBN). One or two or more of the polymerization initiators can be used alone or in combination. The addition amount of the polymerization initiator is not particularly limited as long as it is sufficient to promote the copolymerization reaction of the monomer, for example, 10 ppm to 7000 ppm relative to the total monomer weight of the polymerization component is preferable.

The step of obtaining the copolymer can be carried out by putting the monomer mixture into a molding mold of metal, glass, plastic and the like, sealing, raising the temperature in the range of 25° C. to 120° C. in a stepwise or continuous manner in a thermostatic oven, and completing the polymerization in 5 hours to 120 hours. Ultraviolet rays, electron beams, gamma rays and the like can be used for the polymerization. In addition, a solution polymerization can be applied by adding water or an organic solvent to the monomer mixture.

In the step of obtaining the hydrogel, the polymer is cooled to room temperature after the polymerization is completed, the resulting polymer is peeled off from the molding mold, and after cutting and polishing as necessary, the hydrogel is hydrated and swollen to become hydrogel. Examples of the liquid (swelling liquid) used include water, physiological saline, isotonic buffer. The swelling liquid is heated to 60° C.-100° C. and soaked for a certain period of time to achieve a swollen state. In addition, it is preferable to remove the unpolymerized monomer contained in the polymer at the time of swelling treatment.

The present invention will now be described more specifically with reference to the following Examples, which are not intended to limit the present invention. The present invention may take various forms to the extent that the objectives of the present invention are achieved.

EXAMPLES

Example 1. Synthesis of Triptycene Derivative (6)

1. Synthesis Scheme for Triptycene Derivative (6)

A triptycene derivative (6) was synthesized according to the following Scheme (I):

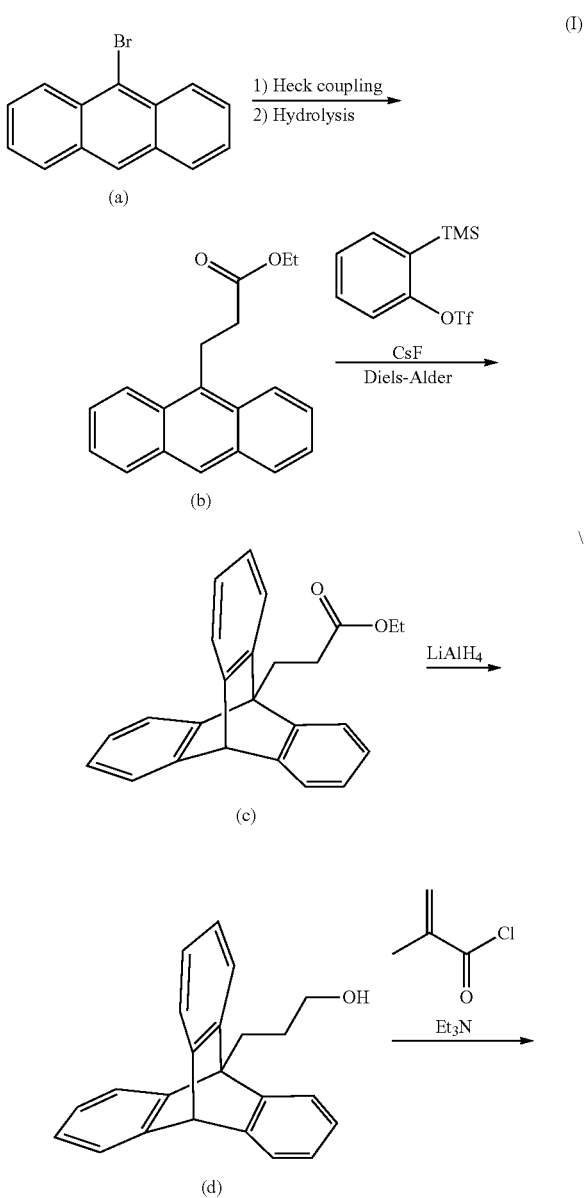

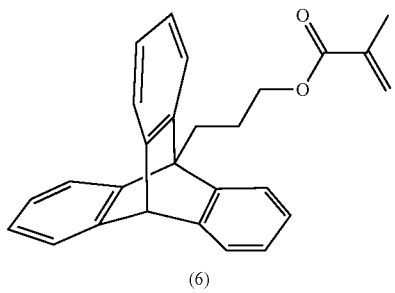

(6)

2. Synthesis of Compound (b)

Compound (b) in Scheme (I) was synthesized according to a method described in Ke Pan, et al., Journal of Organometallic Chemistry, 2008; 693(17); p. 2863-2868, the disclosure of which is incorporated herein by reference in its entirety. Specifically, to a dimethylformamide solution (30 ml) of 2.7 g (10 mmol) of compound (a), which is 9-bromoanthracene, 0.19 g (0.2 mmol) of Herrmann's palladacycle, 2.1 g (15 mmol) of potassium carbonate, and 2.3 mL (15 mmol) of acrolein diethyl acetal were added under an argon atmosphere at room temperature and the mixture was stirred overnight at 110° C. to allow the reaction to proceed. The resulting reaction mixture was allowed to cool to room temperature and diluted with ethyl acetate. This was followed by washing with 1N hydrochloric acid, a saturated aqueous sodium bicarbonate solution and a saturated brine. The separated organic layer was dried over anhydrous magnesium sulfate and the solvent was removed by evaporation. The resulting residue was purified by silica gel column chromatography to obtain 2.4 g (87% yield) of compound (b).

3. Synthesis of Compound (c)

To a solution of 0.87 g (3.1 mmol) of compound (b) dissolved in 15 ml acetonitrile, 0.57 g (3.7 mmol) of cesium fluoride and 0.91 mL (3.7 mmol) of 2-(trimethylsilyl)phenyl triflate were added under an argon atmosphere and the mixture was stirred at 40° C. for 18 hours. After stirring, the reaction mixture was allowed to cool to room temperature and filtrated through Celite. The resulting filtrate was concentrated under reduced pressure. The resulting residue was purified by silica gel column chromatography to obtain 0.92 g (83% yield) of compound (c).

NMR spectra for the resulting compound (c) were as follows:

$^1$H-NMR (CDCl$_3$) δ ppm; 1.35 (t, 3H), 3.17 (m, 2H), 3.35 (m, 2H), 4.31 (q, 2H), 5.35 (s, 1H), 7.00 (m, 6H), 7.37 (m, 6H)

$^{13}$C-NMR (CDCl$_3$) δ ppm; 14.47, 22.61, 30.96, 53.48, 54.58, 61.01, 122.12, 123.70, 125.02, 125.14, 145.76, 146.99, 174.20

4. Synthesis of Compound (d)

0.20 g (5.3 mmol) of lithium aluminum hydride was dissolved in 15 mL tetrahydrofuran chilled to 0° C. under an argon atmosphere to form a solution. To the resulting solution, 1.56 g (4.4 mmol) of compound (c) was added and the mixture was stirred for three hours at room temperature. While the resulting reaction mixture was chilled on ice, 0.2 mL water, a 0.2 mL 15 w/v % aqueous sodium hydroxide solution, and 0.6 mL water were sequentially added dropwise slowly and the mixture was stirred for one hour at room temperature. After stirring, the reaction mixture was filtrated through Celite. The resulting filtrate was concentrated under reduced pressure. The resulting residue was purified by silica gel column chromatography to obtain 1.34 g (98% yield) of compound (d).

NMR spectra for the resulting compound (d) were as follows:

$^1$H-NMR (CDCl$_3$) δ ppm; 2.41 (m, 2H), 2.98 (m, 2H), 4.00 (t, 2H), 5.34 (s, 1H), 6.96 (m, 6H), 7.36 (m, 6H).

$^{13}$C-NMR (CDCl$_3$) δ ppm; 24.36, 28.23, 53.29, 54.63, 64.00, 122.44, 123.60, 124.88, 124.98, 146.33, 147.07.

5. Synthesis of Triptycene Derivative (6)

To a solution of 1.34 g (4.3 mmol) of compound (d) dissolved in 20 mL tetrahydrofuran, 0.90 mL (6.5 mmol) triethylamine and 0.61 mL (6.5 mmol) methacryloyl chloride were added under an argon atmosphere at 0° C. and the mixture was stirred at 0° C. for 18 hours. After stirring, the reaction was quenched by adding a saturated aqueous sodium bicarbonate solution and the organic compound in the solution was extracted with diethyl ether. The extracted organic layer was washed with saturated brine and dried with anhydrous magnesium sulfate. The solvent was then removed from the dried organic layer by evaporation and the resulting residue was purified by silica gel column chromatography to obtain 1.03 g (63% yield) of a triptycene derivative (6).

NMR spectra for the resulting triptycene derivative (6) were as follows:

$^1$H-NMR (CDCl$_3$) δ ppm; 2.04 (s, 3H), 2.60 (m, 2H), 3.04 (m, 2H), 4.58 (t, 2H), 5.36 (s, 1H), 5.63 (m, 1H), 6.25 (s, 1H), 6.99 (m, 6H), 7.39 (m, 6H).

$^{13}$C-NMR (CDCl$_3$) δ ppm; 18.60, 24.53, 24.57, 53.15, 54.62, 65.64, 122.28, 123.68, 124.91, 125.07, 125.85, 136.50, 146.09, 147.04, 167.77.

Example 2. Synthesis of Triptycene Derivative (7)

1. Synthesis Scheme for Triptycene Derivative (7)

A triptycene derivative (7) was synthesized according to the following Scheme (II):

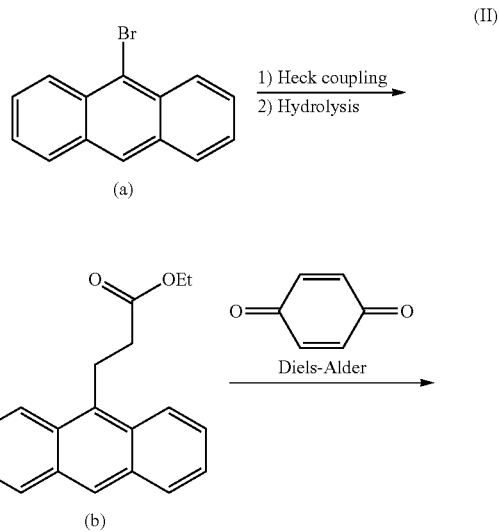

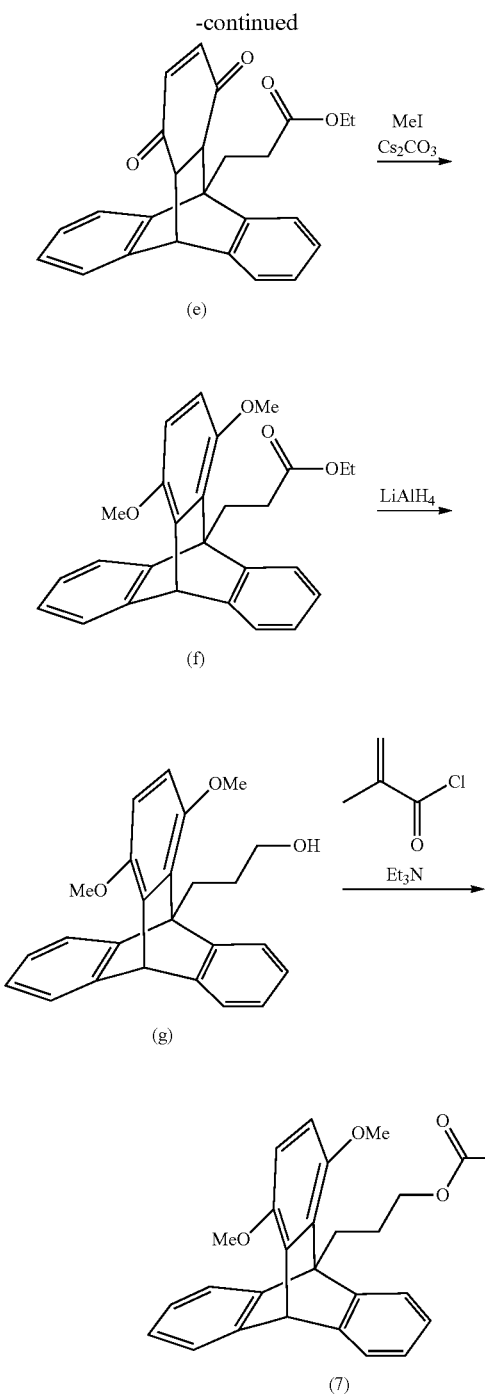

(e)

(f)

(g)

(7)

2. Synthesis of Compound (b)
Compound (b) was synthesized with reference to "2. Synthesis of compound (b)" in Example 1.

3. Synthesis of Compound (e)
To a solution of 1.1 g (10 mmol) of benzoquinone dissolved in 15 mL dichrolomethane, 1.1 mL (9.0 mmol) of a boron trifluoride-diethyl ether complex was added under an argon atmosphere at 0° C. and the mixture was stirred for 30 min. After stirring, the reaction mixture was cooled to −20° C. To the cooled reaction mixture, 0.56 g (2.0 mmol) of compound (b) was added and the mixture was stirred for three hours at −20° C. After stirring, the reaction mixture was allowed to cool to room temperature and washed with saturated brine. The organic layer separated from the washed reaction mixture was then dried over anhydrous magnesium sulfate. The solvent was removed from the dried organic layer by evaporation and the resulting residue was purified by silica gel column chromatography to obtain 0.67 g (87% yield) of compound (e).

NMR spectra for the resulting compound (e) were as follows:

$^1$H-NMR (CDCl$_3$) δ ppm; 1.37 (t, 3H), 2.80 (m, 2H), 2.90 (m, 1H), 2.99 (d, 1H), 3.22 (dd, 1H), 3.34 (m, 1H), 4.29 (dd, 2H), 4.65 (d, 1H), 6.12 (d, 2H), 7.18 (m, 6H), 7.41 (m, 2H).

$^{13}$C-NMR (CDCl$_3$) δ ppm; 14.48, 24.00, 30.22, 49.38, 50.10, 51.05, 60.86, 122.24, 123.17, 124.20, 124.93, 126.63, 126.73, 126.85, 127.06, 139.03, 140.05, 141.37, 141.88, 142.98, 173.85, 197.73, 198.89.

4. Synthesis of Compound (f)
To a solution of 0.93 g (2.4 mmol) of compound (e) dissolved in 10 mL dimethylformamide, 2.0 g (6.0 mmol) of cesium carbonate and 0.67 mL (7.2 mmol) methyl iodide were added under an argon atmosphere and the mixture was stirred at 40° C. for 18 hours. After stirring, the reaction mixture was filtered through Celite. The resulting filtrate was concentrated under reduced pressure and the resulting concentrated residue was purified by silica gel column chromatography to obtain 0.82 g (82% yield) of compound (f).

NMR spectra for the resulting compound (f) were as follows:

$^1$H-NMR (CDCl$_3$) δ ppm; 1.37 (t, 3H), 3.09 (br s, 2H), 3.66 (s, 3H), 3.74 (br s, 2H), 3.80 (s, 3H), 4.29 (q, 2H), 5.86 (s, 1H), 6.51 (m, 2H), 7.01 (m, 4H), 7.43 (m, 4H).

$^{13}$C-NMR (CDCl$_3$) δ ppm; 14.52, 24.23, 32.65, 32.71, 47.27, 56.08, 56.50, 60.47, 109.73, 110.23, 123.47, 123.79, 124.78, 125.21, 125.55, 146.50, 148.86, 150.17, 174.92.

5. Synthesis of Compound (g)
The same procedure was followed as in "4. Synthesis of compound (d)" in Example 1, except that 0.69 g (1.7 mmol) of compound (f) was used in place of compound (c) to obtain 0.58 g (93% yield) of compound (g).

NMR spectra for the resulting compound (g) were as follows:

$^1$H-NMR (CDCl$_3$) δ ppm; 1.65 (br s, 1H), 2.34 (br s, 2H), 3.28 (br s, 2H), 3.70 (s, 3H), 3.79 (s, 3H), 4.05 (t, 2H), 5.85 (s, 1H), 6.50 (m, 2H), 7.01 (m, 4H), 7.46 (m, 4H).

$^{13}$C-NMR (CDCl$_3$) δ ppm; 26.06, 29.85, 29.99, 47.38, 56.56, 56.60, 64.70, 109.68, 110.72, 123.76, 124.66, 124.91, 146.67, 148.94, 150.45.

6. Synthesis of Triptycene Derivative (7)
The same procedure was followed as in "5. Synthesis of triptycene derivative (6)" in Example 1, except that 0.58 g (1.6 mmol) of compound (g) was used in place of compound (d) to obtain 0.62 g (90% yield) of triptycene derivative (7).

NMR spectra for the resulting triptycene derivative (7) were as follows.

$^1$H-NMR (CDCl$_3$) δ ppm; 2.04 (m, 3H), 2.47 (br s, 2H), 3.33 (br s, 2H), 3.70 (s, 3H), 3.78 (s, 3H), 4.54 (t, 2H), 5.62 (m, 1H), 5.86 (s, 1H), 6.23 (d, 1H), 6.50 (br s, 2H), 7.02 (m, 4H), 7.41 (br s, 2H), 7.50 (br s, 2H).

$^{13}$C-NMR (CDCl$_3$) δ ppm; 18.59, 25.91, 26.30, 47.35, 54.86, 56.32, 56.54, 660.33, 109.66, 110.47, 123.78, 124.66, 124.96, 125.54, 136.70, 138.11, 146.66, 148.88, 150.37, 167.87.

Example 3. Synthesis of Triptycene Derivative (8)

1. Synthesis Scheme for Triptycene Derivative (8)

A triptycene derivative (8) was synthesized according to the following Scheme (III):

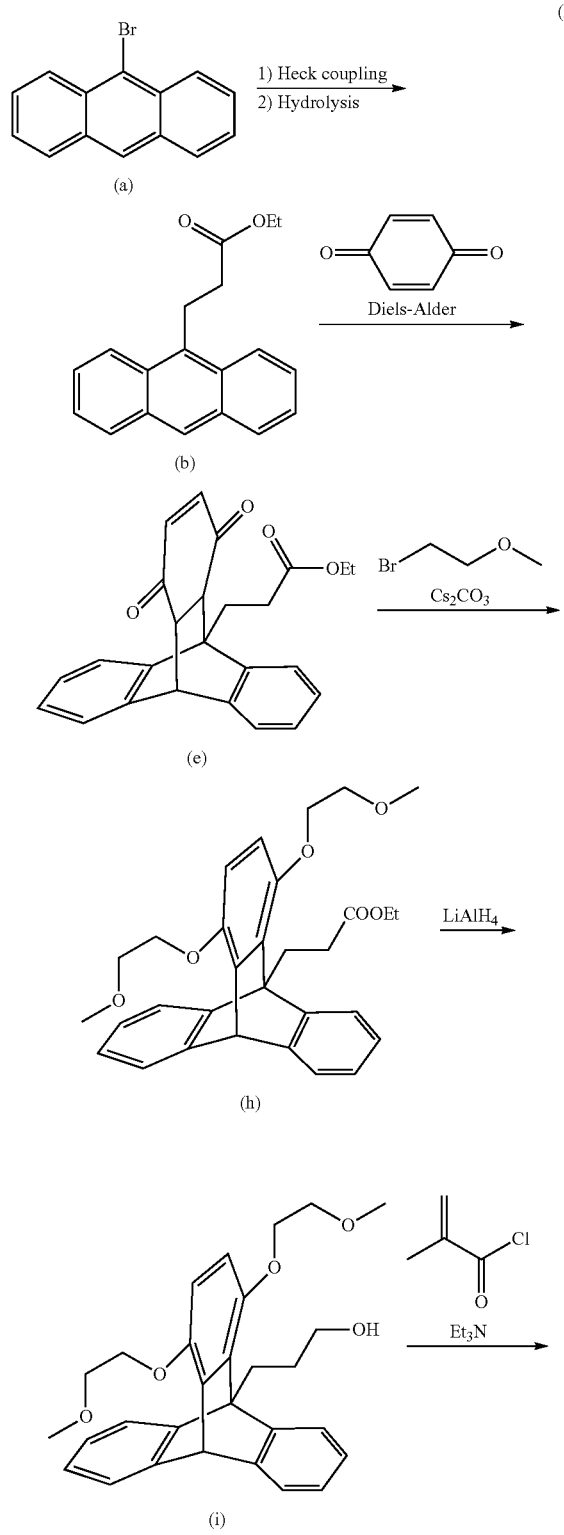

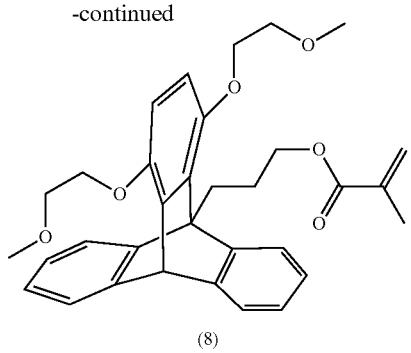

(8)

2. Synthesis of Compound (b)

Compound (b) was synthesized with reference to "2. Synthesis of compound (b)" in Example 1.

3. Synthesis of Compound (e)

Compound (e) was synthesized with reference to "3. Synthesis of compound (e)" in Example 2.

4. Synthesis of Compound (h)

To a solution of 0.50 g (1.3 mmol) of compound (e) dissolved in 10 mL dimethylformamide, 1.1 g (3.2 mmol) of cesium carbonate and 0.37 mL (3.9 mmol) of 2-methoxyethyl bromide were added under an argon atmosphere and the mixture was stirred at 40° C. for 18 hours. After stirring, the reaction mixture was filtrated through Celite. The resulting filtrate was concentrated under reduced pressure and the resulting concentrated residue was purified by silica gel column chromatography to obtain 0.57 g (87% yield) of compound (h).

NMR spectra for the resulting compound (h) were as follows:

$^1$H-NMR (CDCl$_3$) δ ppm; 1.29 (t, 3H), 2.98 (m, 2H), 3.38 (br s, 3H), 3.45 (s, 3H), 3.70 (m, 6H), 3.92 (m, 2H), 4.00 (m, 2H), 4.22 (q, 2H), 5.81 (s, 1H), 6.44 (s, 2H), 6.94 (m, 4H), 7.38 (m, 4H).

$^{13}$C-NMR (CDCl$_3$) δ ppm; 14.55, 24.37, 32.09, 47.45, 59.20, 59.41, 60.55, 69.25, 69.89, 71.22, 71.39, 112.36, 123.56, 123.89, 124.80, 125.18, 146.40, 148.25, 149.90, 174.92.

5. Synthesis of Compound (i)

Compound (i) 0.41 g (97% yield) was obtained with reference to "4. Synthesis of compound (d)" in Example 1, except that 0.46 g (0.92 mmol) of compound (h) was used in place of compound (c).

NMR spectra for the resulting compound (i) were as follows:

$^1$H-NMR (CDCl$_3$) δ ppm; 2.36 (br s, 2H), 3.46 (br s, 2H), 3.47 (s, 3H), 3.52 (s, 3H), 3.76 (dd, 4H), 4.03 (m, 4H), 5.88 (s, 1H), 6.46 (d, 1H), 6.52 (d, 1H), 7.00 (m, 4H), 7.40 (d, 2H), 7.51 (d, 2H).

$^{13}$C-NMR (CDCl$_3$) δ ppm; 26.44, 29.14, 47.54, 58.85, 59.41, 64.48, 68.92, 69.89, 71.39, 71.69, 112.39, 123.81, 124.66, 124.93, 146.46, 148.42, 149.88.

6. Synthesis of Triptycene Derivative (8)

The same procedure was followed as in "5. Synthesis of triptycene derivative (6)" in Example 1, except that 0.71 g (1.5 mmol) of compound (i) was used in place of compound (d) to obtain 0.63 g (77% yield) of triptycene derivative (8).

NMR spectra for the resulting triptycene derivative (8) were as follows.

$^1$H-NMR (CDCl$_3$) δ ppm; 2.04 (m, 3H), 2.51 (br s, 2H), 3.44 (m, 5H), 3.52 (s, 3H), 3.71 (t, 2H), 3.77 (m, 2H), 3.97

(m, 2H), 4.06 (m, 2H), 4.53 (t, 2H), 5.62 (m, 1H), 5.88 (s, 1H), 6.24 (m, 1H), 6.51 (m, 2H), 7.03 (m, 4H), 7.41 (m, 2H), 7.53 (br s, 2H).

$^{13}$C-NMR (CDCl$_3$) δ ppm; 14.26, 18.61, 22.78, 25.43, 26.16, 31.71, 47.53, 59.39, 66.22, 69.92, 71.39, 112.34, 112.44, 123.87, 124.64, 124.98, 125.58, 136.67, 146.51, 148.24, 150.02, 167.87.

Example 4. Synthesis of Triptycene Derivatives (9) and (10)

1. Synthesis Scheme for Triptycene Derivatives (9) and (10)

Triptycene derivatives (9) and (10) were synthesized according to the following Scheme (IV):

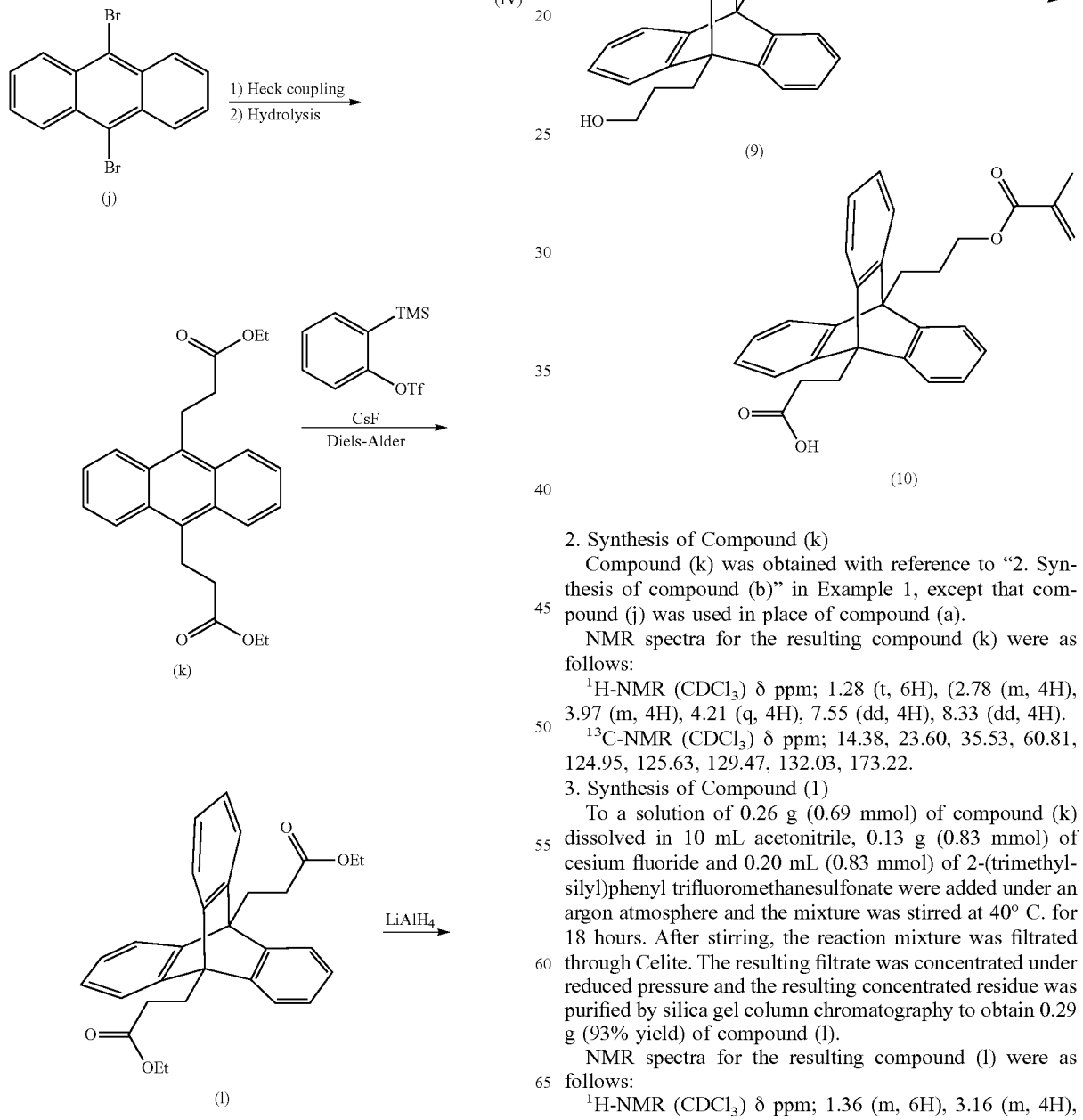

2. Synthesis of Compound (k)

Compound (k) was obtained with reference to "2. Synthesis of compound (b)" in Example 1, except that compound (j) was used in place of compound (a).

NMR spectra for the resulting compound (k) were as follows:

$^1$H-NMR (CDCl$_3$) δ ppm; 1.28 (t, 6H), (2.78 (m, 4H), 3.97 (m, 4H), 4.21 (q, 4H), 7.55 (dd, 4H), 8.33 (dd, 4H).

$^{13}$C-NMR (CDCl$_3$) δ ppm; 14.38, 23.60, 35.53, 60.81, 124.95, 125.63, 129.47, 132.03, 173.22.

3. Synthesis of Compound (l)

To a solution of 0.26 g (0.69 mmol) of compound (k) dissolved in 10 mL acetonitrile, 0.13 g (0.83 mmol) of cesium fluoride and 0.20 mL (0.83 mmol) of 2-(trimethylsilyl)phenyl trifluoromethanesulfonate were added under an argon atmosphere and the mixture was stirred at 40° C. for 18 hours. After stirring, the reaction mixture was filtrated through Celite. The resulting filtrate was concentrated under reduced pressure and the resulting concentrated residue was purified by silica gel column chromatography to obtain 0.29 g (93% yield) of compound (l).

NMR spectra for the resulting compound (l) were as follows:

$^1$H-NMR (CDCl$_3$) δ ppm; 1.36 (m, 6H), 3.16 (m, 4H), 3.34 (m, 4H), 4.33 (q, 4H), 7.02 (m, 6H) 7.40 (m, 6H).

$^{13}$C-NMR (CDCl$_3$) δ ppm; 14.47, 22.75, 31.03, 52.76, 61.04, 122.19, 124.88, 146.91, 174.18.

4. Synthesis of Compound (m)

Compound (m) 0.34 g (93% yield) was obtained with reference to "4. Synthesis of compound (d)" in Example 1, except that 0.45 g (1.0 mmol) of compound (l) was used in place of compound (c).

NMR spectra for the resulting compound (m) were as follows:

$^1$H-NMR (CDCl$_3$) δ ppm; 2.49 (m, 4H), 3.00 (m, 4H), 4.13 (m, 4H), 7.00 (br s, 6H), 7.43 (br s, 6H).

$^{13}$C-NMR (CDCl$_3$) δ ppm; 24.59, 28.37, 52.50, 64.16, 122.29, 124.63.

5. Synthesis of Triptycene Derivative (9)

To a solution of 50 mg (0.14 mmol) of compound (m) dissolved in 5 mL tetrahydrofuran, 5.4 mg (0.14 mmol) of sodium hydride was added under an argon atmosphere at 0° C. and the mixture was stirred at 0° C. for 30 minutes. Methacryloyl chloride 12 μL (0.13 mmol) was added to the mixture and the mixture was stirred at 0° C. for 18 hours. After stirring, the reaction was quenched by adding a saturated aqueous sodium bicarbonate solution and the organic compound in the solution was extracted with diethyl ether. The extracted organic layer was washed with saturated brine and dried with anhydrous magnesium sulfate. The solvent was then removed from the dried organic layer by evaporation and the resulting residue was purified by silica gel column chromatography to obtain 38 mg (64% yield) of a triptycene derivative (9).

NMR spectra for the resulting compound (9) were as follows:

$^1$H-NMR (CDCl$_3$) δ ppm; 1.62 (br s, 1H), 2.05 (s, 3H), 2.47 (m, 2H), 2.61 (m, 2H), 3.01 (dd, 4H), 4.13 (t, 2H), 4.59 (t, 2H), 5.63 (s, 1H), 6.25 (s, 1H), 7.01 (s, 6H), 7.43 (br s, 6H).

$^{13}$C-NMR (CDCl$_3$) δ ppm; 18.57, 24.60, 24.78, 28.34, 52.38, 52.52, 61.57, 61.14, 65.70, 122.34, 124.78, 125.94, 167.94.

6. Synthesis of Triptycene Derivative (10)

Jones reagent was dropped into a solution of 27 mg (0.06 mmol) of triptycene derivative (9) dissolved 1 mL acetone at 0° C. until the solution turned orange. After the solution was stirred for 10 minutes, and the resulting organic material was extracted with diethyl ether three times. The extracted organic layer was washed with saturated brine and dried with anhydrous magnesium sulfate. The solvent was then removed from the dried organic layer by evaporation and the resulting residue was purified by silica gel column chromatography to obtain 9.9 mg (36% yield) of a triptycene derivative (10).

NMR spectra for the resulting triptycene derivative (10) were as follows:

$^1$H-NMR (CDCl$_3$) δ ppm; 2.04 (m, 3H), 2.62 (m, 2H), 3.04 (m, 2H), 3.30 (d, 2H), 3.38 (d, 2H), 4.60 (t, 2H), 5.65 (s, 1H), 6.26 (s, 1H), 7.05 (br s, 6H), 7.42 (br s, 6H).

$^{13}$C-NMR (CDCl$_3$) δ ppm; 18.57, 22.59, 24.58, 30.60, 52.44, 65.67, 122.09, 124.98, 125.98, 135.60, 147.31, 150.29, 158.26, 160.24, 167.96.

Example 5. Synthesis of Triptycene Derivative (11)

1. Synthesis Scheme for Triptycene Derivative (11)

A triptycene derivative (11) was synthesized according to the following Scheme (V):

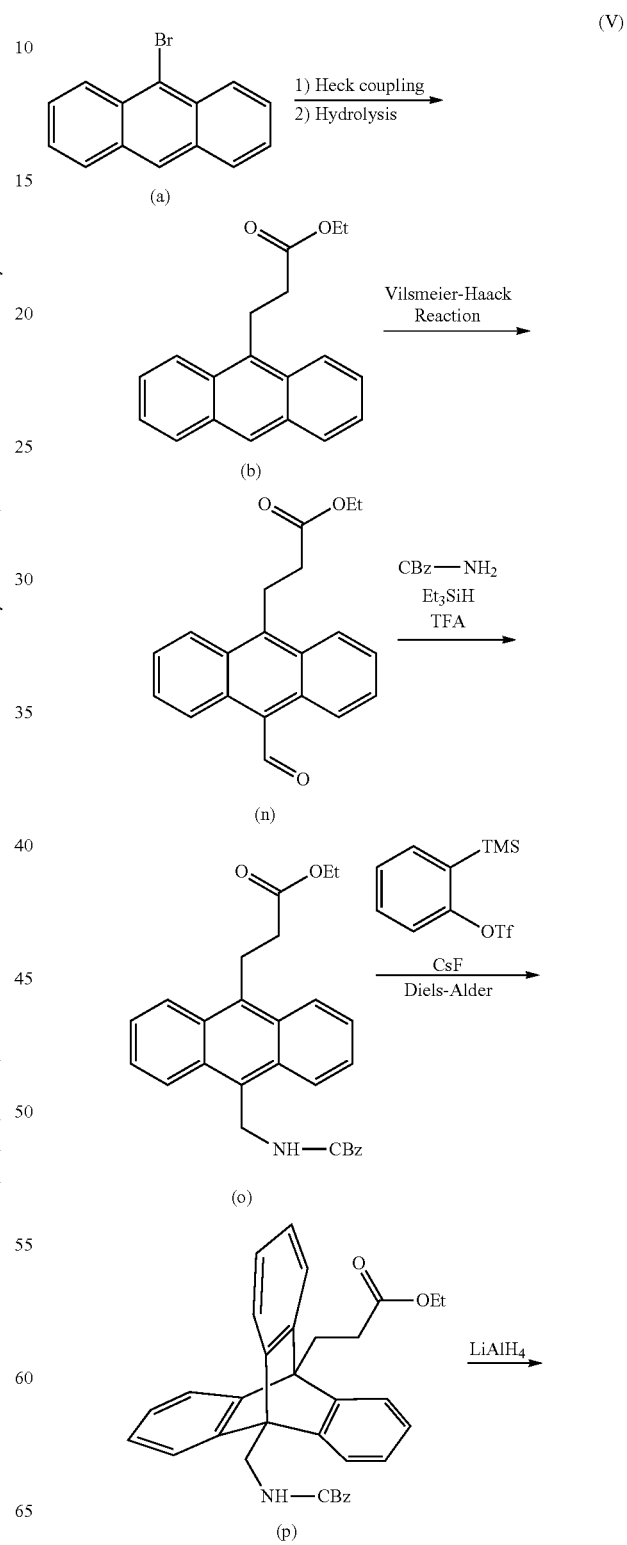

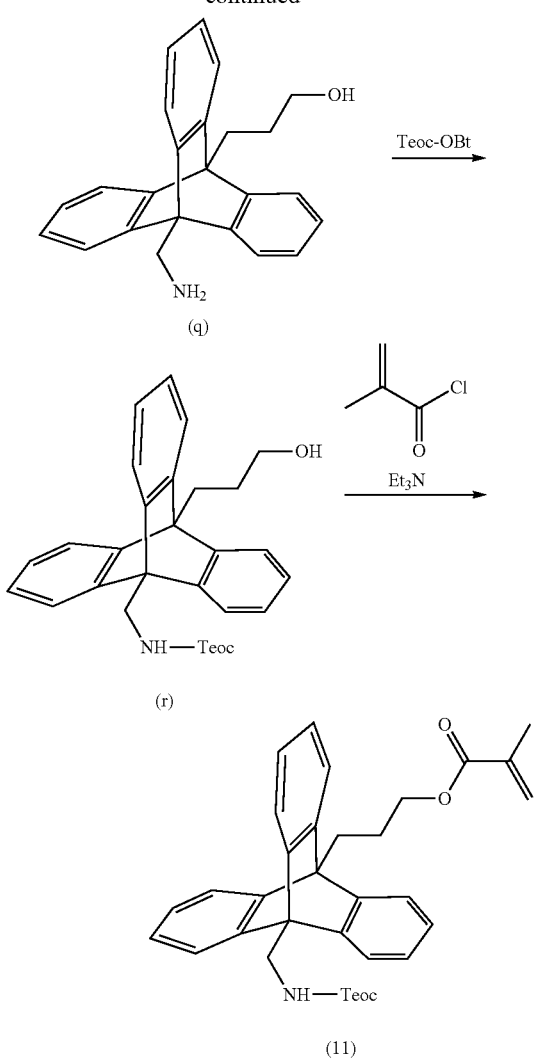

(q)

(r)

(11)

2. Synthesis of Compound (b)

Compound (b) was synthesized with reference to "2. Synthesis of compound (b)" in Example 1.

3. Synthesis of Compound (n)

To 5 mL of dimethylformamide, 0.94 mL (10.1 mmol) of phosphoryl chloride was added dropwise under an argon atmosphere at 0° C. and the mixture was stirred at room temperature for 1.5 hours. To the stirred reaction mixture, 1.0 g (3.6 mmol) of compound (b) was dissolved and the mixture was stirred at 110° C. for 18 hours. After stirring, the reaction mixture was allowed to cool to room temperature and diluted with ethyl acetate. The diluted reaction mixture was sequentially washed with 1N hydrochloric acid, a saturated aqueous sodium bicarbonate solution and a saturated brine. The organic layer separated after washing was dried over anhydrous magnesium sulfate. The solvent was removed from the dried organic layer by evaporation and the resulting residue was purified by silica gel column chromatography to obtain 0.78 g (71% yield) of compound (n).

NMR spectra for the resulting compound (n) were as follows:

$^1$H-NMR (CDCl$_3$) δ ppm; 1.25 (m, 3H), 2.77 (m, 2H), 3.98 (m, 2H), 4.20 (q, 2H), 7.62 (m, 4H), 8.33 (m, 2H), 8.92 (dd, 2H), 11.45 (s, 1H).

$^{13}$C-NMR (CDCl$_3$) δ ppm; 14.34, 24.19, 35.32, 60.99, 124.45, 124.77, 125.01, 126.30, 128.48, 129.08, 131.64, 141.68, 172.65, 193.63.

4. Synthesis of Compound (o)

To a solution dissolved 0.74 g (2.4 mmol) of compound (n) in 10 mL of acetonitrile, 1.1 g (7.2 mmol) of benzyl carbamate, 0.59 mL (7.2 mmol) of triethylsilane and 0.61 mL (7.0 mmol) of trifluoroacetic acid were added dropwise under an argon atmosphere and the mixture was stirred at room temperature for 18 hours. After stirring, the reaction mixture was diluted with ethyl acetate. The diluted reaction mixture was sequentially washed with a saturated sodium hydrogen carbonate solution and a saturated saline. The organic layer separated after washing was dried over anhydrous magnesium sulfate. The solvent was removed from the dried organic layer by evaporation and the resulting residue was purified by silica gel column chromatography to obtain 0.84 g (83% yield) of compound (o).

NMR spectra for the resulting compound (o) were as follows:

$^1$H-NMR (CDCl$_3$) δ ppm; 1.21 (m, 3H), 2.69 (m, 2H), 3.90 (m, 2H), 4.13 (q, 2H), 4.94 (s, 1H), 5.08 (s, 2H), 5.32 (d, 2H), 7.28 (m, 5H), 7.50 (m, 4H), 8.27 (m, 4H).

$^{13}$C-NMR (CDCl$_3$) δ ppm; 14.36, 23.60, 35.40, 37.73, 60.84, 67.00, 124.84, 125.82, 126.36, 128.16, 128.60, 129.38, 130.19, 134.17, 136.52, 156.23, 173.02.

5. Synthesis of compound (p) The same procedure was followed as in "3. Synthesis of compound (c)" in Example 1, except that 0.29 g (0.66 mmol) of compound (o) used in place of compound (b) to obtain 0.27 g (78% yield) of compound (p).

NMR spectra for the resulting compound (p) were as follows:

$^1$H-NMR (CDCl$_3$) δ ppm; 1.36 (m, 3H), 3.14 (m, 2H), 3.34 (m, 2H), 4.33 (q, 2H), 4.85 (d, 2H), 5.26 (s, 2H), 5.42 (m, 1H), 7.03 (m, 6H), 7.35 (m, 11H).

$^{13}$C-NMR (CDCl$_3$) δ ppm; 14.48, 22.68, 30.97, 40.20, 52.03, 52.92, 61.11, 67.19, 122.35, 125.26, 128.20, 128.33, 128.69, 136.58, 147.07, 165.9, 174.08.

6. Synthesis of Compound (q)

The same procedure was followed as in "4. Synthesis of compound (d)" in Example 1, except that 0.15 g (0.29 mmol) of compound (p) used in place of compound (c) to obtain 87 mg (88% yield) of compound (q).

NMR spectra for the resulting compound (q) were as follows:

$^1$H-NMR (CDCl$_3$) δ ppm; 2.45 (m, 2H), 3.03 (m, 2H), 4.11 (d, 2H), 4.91 (d, 2H), 6.29 (s, 1H), 7.02 (br s, 6H), 7.39 (m, 6H), 8.41 (s, 1H).

$^{13}$C-NMR (CDCl$_3$) δ ppm; 24.47, 28.19, 37.44, 51.49, 52.71, 63.89, 121.92, 125.10, 161.69.

7. Synthesis of Triptycene Derivative (11)

To a solution of 25 mg (0.073 mmol) of compound (q) dissolved in 1 mL dichloromethane, 22 mg (0.080 mmol) of 1-[2-(trimethylsilyl) ethoxycarbonyloxy] benzotriazole was added under an argon atmosphere and the mixture was stirred at room temperature for 30 minutes. The reaction was quenched by adding 5% aqueous sodium bicarbonate solution and the organic compound in the solution was extracted with dichloromethane. The extracted organic layer was washed with 5% aqueous sodium bicarbonate solution and dried with anhydrous magnesium sulfate. Compound (r) was obtained by removing the solvent from the dried organic layer. To a solution of resulting compound (r) dissolved in 5 mL tetrahydrofuran, 20 μL (0.14 mmol) of triethylamine and 14 μL (0.14 mmol) of methacryloyl chloride were added under an argon atmosphere and the mixture was stirred at 0°

C. for 18 hours. After stirring, the reaction was quenched by adding a saturated aqueous sodium bicarbonate solution and the organic compound in the solution was extracted with diethyl ether. The extracted organic layer was washed with saturated brine and dried with anhydrous magnesium sulfate. The solvent was then removed from the dried organic layer by evaporation and the resulting residue was purified by silica gel column chromatography to obtain 6.5 mg (18% yield) of a triptycene derivative (11).

NMR spectra for the resulting triptycene derivative (11) were as follows:

$^1$H-NMR (CDCl$_3$) δ ppm; 0.07 (s, 9H), 1.67 (m, 4H), 2.04 (s, 3H), 2.59 (m, 2H), 3.05 (m, 2H), 4.60 (t, 2H), 4.93 (d, 2H), 5.65 (s, 1H), 6.25 (s, 1H), 7.06 (m, 6H), 7.41 (m, 6H), 8.46 (s, 1H).

$^{13}$C-NMR (CDCl$_3$) δ ppm; 0.06, 1.10, 18.57, 24.53, 31.04, 37.40, 51.56, 52.61, 64.17, 65.55, 122.04, 125.30, 126.01, 136.57, 161.72, 167.90.

Example 6. Synthesis of Triptycene Derivative (12)

1. Synthesis Scheme for Triptycene Derivative (12)

A triptycene derivative (12) was synthesized according to the following Scheme (VI):

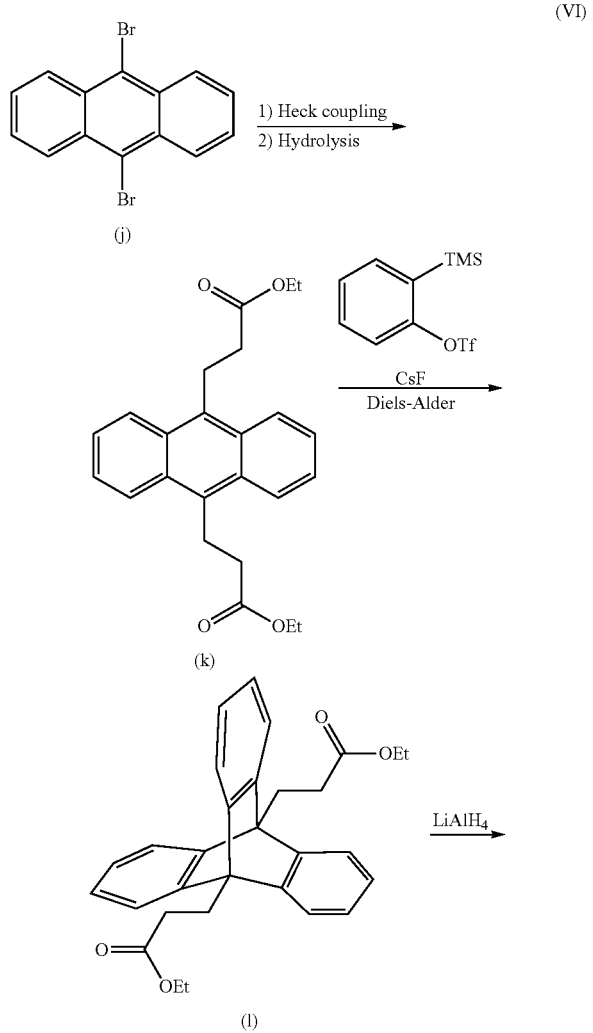

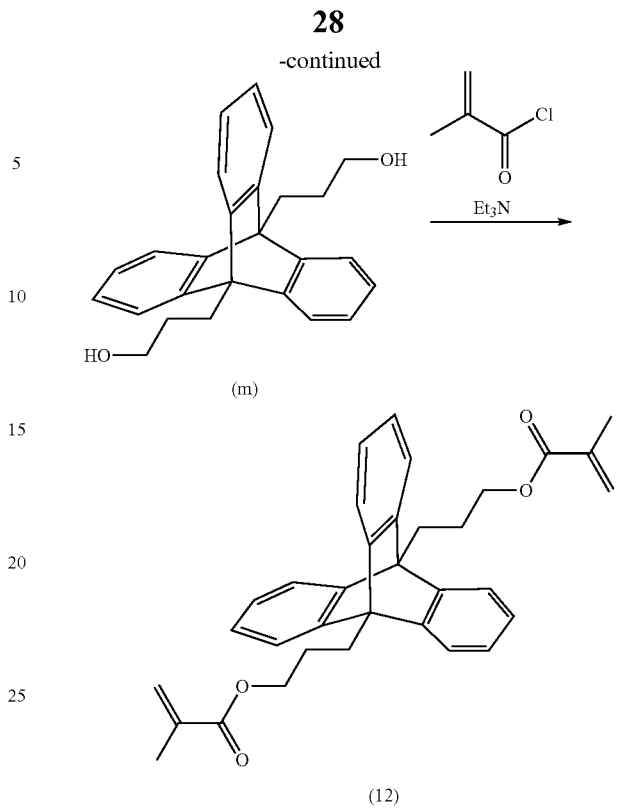

2. Synthesis of Compound (k)

Compound (k) was synthesized with reference to "2. Synthesis of compound (k)" in Example 4.

3. Synthesis of Compound (l)

Compound (l) was synthesized with reference to "3. Synthesis of compound (l)" in Example 4.

4. Synthesis of Compound (m)

Compound (m) was synthesized with reference to "4. Synthesis of compound (m)" in Example 4.

5. Synthesis of Triptycene Derivative (12)

To a solution of 35 mg (0.094 mmol) of compound (m) dissolved in 5 mL tetrahydrofuran, 33 μL (0.24 mmol) of triethylamine and 22 μL (0.24 mmol) of methacryloyl chloride were added under an argon atmosphere at 0° C. and the mixture was stirred at 0° C. for 18 hours. After stirring, the reaction was quenched by adding a saturated aqueous sodium bicarbonate solution and the organic compound in the solution was extracted with diethyl ether. The extracted organic layer was washed with saturated brine and dried with anhydrous magnesium sulfate. The solvent was then removed from the dried organic layer by evaporation and the resulting residue was purified by silica gel column chromatography to obtain 26 mg (54% yield) of a triptycene derivative (12).

NMR spectra for the resulting triptycene derivative (12) were as follows:

$^1$H-NMR (CDCl$_3$) δ ppm; 2.05 (d, 6H), 2.60 (m, 4H), 3.02 (m, 4H), 4.60 (t, 4H), 5.64 (m, 2H), 6.25 (s, 2H), 7.02 (m, 6H), 7.43 (s, 6H).

$^{13}$C-NMR (CDCl$_3$) δ ppm; 18.56, 24.57, 24.75, 52.39, 65.67, 122.41, 124.80, 125.93, 136.60, 167.91.

Example 7. Formation of Polymer Hydrogel Containing Triptycene Derivatives (9), (10), (11) and (12) Obtained by Examples 4-6

A monomer mixture was obtained by mixing 0.5 g of each of the triptycene derivative compounds (9)-(12) synthesized in Example 1, 9.5 g of 2-hydroxyethyl methacrylate, 0.01 g of ethylene glycol dimethacrylate, and 2000 ppm of azobisisobutyronitrile (AIBN) at room temperature and stirring for about one hour with sufficient nitrogen substitution. After stirring, the monomer mixture was placed in a molding mold and heated to 50° C.-100° C. for 25 hours to obtain the polymer. The resulting polymer was cooled to reach a room temperature, released from the mold, and immersed in distilled water at about 60° C. for about 4 hours to hydrate and swell to obtain triptycene derivative-containing hydrogel of four types.

As a comparative example, the same procedure was followed as in Example 4, except that compound 8 represented by following formula (A) in Patent Document 9 (JP 2008-075407 A) was used in place of compounds (9)-(12) to mix 9.5 g of 2-hydroxyethyl methacrylate, 0.01 g of ethylene glycol dimethacrylate, and 2000 ppm of AIBN. However, a homogeneous solution could not be obtained and it could not be used for the copolymerization reaction, when compound 8 of Patent Document 9 was used. This suggests that the conventional triptycene derivatives have low compatibility with hydrophilic compound.

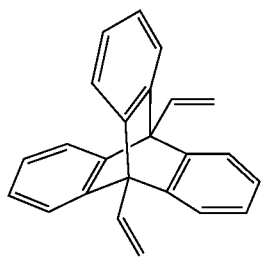

(A)

INDUSTRIAL APPLICABILITY

The polymerizable triptycene derivative in one embodiment of the present invention and the polymer compound as constituent component thereof can be used as materials in a variety of applications, including, for example, liquid crystal alignment films, liquid crystal display elements, organic EL displays, organic thin films with electron transporting properties, light-emitting elements and organic conductive compositions, as well as hydrogels, medical devices, ophthalmic lenses and DDS devices.

The invention claimed is:

1. A polymer compound comprising as constituent component:
a polymerizable triptycene derivative represented by the following general formula (1), and

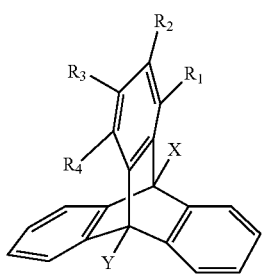

(1)

wherein $R_1$ to $R_4$ are each independently a substituent selected from the group consisting of hydrogen atom, alkyl group, cycloalkyl group, heterocyclic group, alkenyl group, cycloalkenyl group, alkynyl group, alkoxy group, alkylthio group, arylether group, arylthioether group, aryl group, heteroaryl group, halogen atom, carbonyl group, carboxyl group, oxycarbonyl group, carbamoyl group, amino group, phosphineoxide group, and silyl group, with the proviso that adjacent substituents may together form a ring;

one of X and Y is a substituent represented by the following general formula (2):

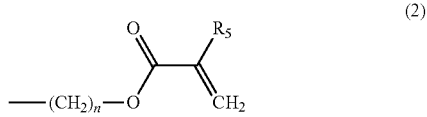

(2)

wherein n is an integer of 1 to 5; and $R_5$ shows hydrogen atom or methyl group and the other of X and Y is a substituent selected from the group consisting of the substituents represented by the general formula (2), hydrogen atom and halogen atom, and protected or unprotected hydroxyl group, hydroxylalkyl group, carboxyl group, carboxylalkyl group, amino group, aminoalkyl group, aminocarbonyl group, aminocarbonylalkyl group, alkoxy group, alkoxyalkyl group, alkoxycarbonyl group, alkoxycarbonylalkyl group, formyl group, formylalkyl group, and alkyl group a compound capable of copolymerizing with the polymerizable triptycene derivative.

2. The polymer compound according to claim 1, wherein the other of X and Y is a substituent selected from the group consisting of the substituents represented by the following general formula (3):

(3)

wherein n is an integer of 1 to 5; and $R_6$ is a substituent selected from the group consisting of hydrogen atom and alkyl group having any one of carbons 1 to 30, the substituents represented by the following general formula (4):

—$(CH_2)_n$—$NHR_7$ (4)

wherein n is an integer of 1 to 5; and $R_7$ is a substituent selected from the group consisting of hydrogen atom and a carbamate protective group, and the substituents represented by the following general formula (5):

—$(CH_2)_n$—OH (5)

wherein n is an integer of 1 to 5.

3. The polymer compound according to claim 1, wherein the compound capable of copolymerizing with the polymerizable triptycene derivative is a hydrophilic compound capable of copolymerizing with at least one polymerizable triptycene derivative.

* * * * *